United States Patent [19]

Myers et al.

[11]  4,229,610

[45]  Oct. 21, 1980

[54] OLEFIN DOUBLE BOND ISOMERIZATION

[75] Inventors: John W. Myers; Dean P. Montgomery, both of Bartlesville, Okla.

[73] Assignee: Phillips Petroleum Company, Bartlesville, Okla.

[21] Appl. No.: 957,607

[22] Filed: Nov. 3, 1978

[51] Int. Cl.$^2$ ............................ C07C 5/24; C07C 5/30
[52] U.S. Cl. .................................. 585/664; 252/441 R
[58] Field of Search ...................... 260/683.2; 585/664

[56]  References Cited

U.S. PATENT DOCUMENTS

| 3,204,009 | 8/1965 | Keith | 585/664 |
| 3,248,449 | 4/1966 | Goble | 585/669 |
| 3,596,927 | 8/1971 | Mitchell | 585/664 |

Primary Examiner—Veronica O'Keefe

[57]  ABSTRACT

Aliphatic monoolefins which can be normal or branched are isomerized at temperatures in the approximate range 500°–1200° F. in presence of a high surface area activated alumina containing a relatively low amount of sodium oxide ($Na_2O$) to form 1-olefin. Generally, from about 0.13 to about 0.39 milliequivalents of $Na_2O$ per gram of the activated alumina containing the $Na_2O$, supplied by such sodium compounds as are disclosed, the activated alumina having a large surface area, i.e., about 300–400 m$^2$ per gram, is used as a catalyst for the isomerization of, say, isomeric n-butenes. Generally, the olefin treated will have from 4 to about 20 carbon atoms per molecule.

5 Claims, No Drawings

OLEFIN DOUBLE BOND ISOMERIZATION

This invention relates to the double bond isomerization of an olefin. In one of its aspects it relates to the selective double bond isomerization of an olefin to form 1-olefin. In a more specific aspect the invention relates to the use of an activated alumina as a catalyst for olefin isomerization as more specifically described herein. Further, the invention relates to the regeneration of a catalyst as described herein.

In one of its concepts the invention provides a process for the isomerization to 1-olefin of an olefin having from 4 to about 20 carbon atoms, e.g., isomeric n-butenes, in the presence of a catalyst essentially consisting of an activated alumina or alumina gel which has been recommended for drying gases and other adsorption processes, the activated alumina or alumina gel having a high surface area in the approximate range of from about 300 to 400 square meters per gram and containing sodium oxide or a derivative of it, and silica, which have been added to the alumina before it has been formed into particles and calcined, the catalysts of the invention containing from about 0.5 to about 6.3 weight percent silica and from about 0.41 to about 1.228 percent sodium oxide (0.13–0.39 milliequivalents of sodium oxide per gram of catalyst), the isomerization being effected at a temperature in the approximate range of from 500° to 1200° F. at a liquid hourly space velocity in the approximate range of from about 0.5 to about 50. In another of its concepts the invention provides a process for regenerating the catalyst which has been used according to the invention by steps comprising purging the catalyst, adding air to the purging fluid to provide approximately 0.5 volume percent oxygen, continuing this operation for about 1 hour, then raising the concentration of oxygen to 1% for about another hour whereupon the oxygen content is raised to about 2% and maintained at this level until the combined concentration of carbon monoxide and carbon dioxide in the purging fluid, e.g., steam, nitrogen, etc., has fallen to about 0.05 percent, discontinuing the addition of air but continuing purging for about another hour prior to resuming the feeding of olefin.

Terminal olefins, also called 1-olefins or alpha-olefins, are useful as reactants for a number of commercially important processes, such as hydroformylation, sulfation, alkylation, and acid oligomerization. In these processes they are more reactive than internal olefins. The homologous series of 1-olefins can be prepared by the thermal cracking of paraffinic hydrocarbons. However, olefins produced by catalytic cracking will generally have close to thermodynamic equilibrium composition, determined by the cracking temperature, for the mixture of normal and branched isomers. These isomers are frequently not easily separated.

Formation of 1-olefins is favored by the use of high temperatures, i.e., the concentration of 1-olefins in an equilibrium mixture of olefins increases with increasing temperature. Elevated temperatures, unfortunately, make skeletal isomerization of normal olefins more probable. Consequently attempts to maximize the yield of 1-olefins are limited by the temperature at which skeletal isomerization becomes excessive.

U.S. Pat. No. 3,204,009, Aug. 31, 1965 discloses the isomerization of normal or branched-chain monoolefins to obtain selectively a desired olefin product while avoiding the formation of undue amounts of other undesirable reaction products by virtue of cracking and skeletal isomerization by contacting olefinic material to be isomerized under isomerization conditions with a catalyst prepared by calcining a composition of alumina and about 0.4 to 8 milliequivalents, preferably about 1 to 7.6 milliequivalents, per gram of said alumina of a compound selected from the group consisting of alkaline metal, i.e., alkali metal and alkaline earth metal oxides and alkaline metal compounds that decompose upon calcination. The disclosure of the patent is incorporated herein by reference.

In the patent, commercially available alumina, Alcoa (F-1) the properties of which are given in column 3 of the patent, and referred to therein as an activated alumina is stated to have been used in the examples of the patent. The following metals are mentioned as having been incorporated into various catalysts used: sodium, potassium, cesium, rubidium and strontium. Viewing Table I of the patent at, say, 800° F., the activity with potassium as the alkali metal supplied into the catalyst increases with increasing temperature. Thus, at 800° F. the activity is 32 at 0.521 meq. of K/g of alumina; 99 at 1.93 meq. The fall off of activity to 87 at 6.38 meq. of K/g of alumina is, of course, expected, this being of the order of 0.25 grams K/g of alumina, a very large amount of covering over the active sites of the alumina. In Table 3 of the patent, in which a different alumina, Alumina B, was used, again the increase of potassium shows an increase of activity.

The data in the runs of the present invention show that as the sodium on the support increases albeit the milliequivalents employed in all tests are quite small, the activity drops off even in the face of increasing surface area of the alumina.

It is an object of this invention to provide a process for isomerizing an olefin. It is another object of the invention to bring about equilibrium concentrations of 1-olefin in a mixture of isomeric olefins. It is another object of the invention to provide a process for shifting of the double bond of, say, a monoolefin while avoiding undesired reactions, e.g., cracking or skeletal isomerization. It is a further object of the invention to provide a method for regenerating an isomerization catalyst, e.g., an alkali metal promoted activated alumina having a relatively high surface area.

Other aspects, concepts, objects and the several advantages of the invention are apparent from a study of this disclosure and the appended claims.

According to the present invention there is provided a process for shifting of the double bond of a monoolefin having from 4 to about 20 carbon atoms to yield 1-olefin which comprises heating said monoolefin at an isomerization temperature in the approximate range 260°–650° C. (500°–1200° F.) sufficient to cause shifting of the double bond while avoiding substantial cracking or skeletal isomerization in the presence of a catalyst or contact mass essentially comprising an activated alumina having a surface area in the approximate range of from about 300 to about 400 square meters per gram and containing sodium oxide in the approximate range 0.13–0.39 milliequivalents of $Na_2O$ per gram of catalyst, and silica in the approximate range of from about 0.5 to about 6.3 weight percent of the catalyst, the sodium oxide having been supplied in the catalyst composition using a compound of sodium which, upon calcination, yields the oxide.

It is important to note that the alkali, sodium oxide or its derivatives, in the catalysts, affects the activity as follows. When the concentration is too low the selectivity of the catalyst suffers in the sense that excessive skeletal isomerization occurs. On the other hand, when the concentration is too high, the activity suffers and the catalyst rapidly loses activity upon regeneration.

An acceptable range for the concentration of alkali in this catalyst is 0.41–1.22 weight percent $Na_2O$; preferably the concentration is 0.54–1.08 weight percent $Na_2O$. In different terms the acceptable concentration of alkali can lie between 0.13–0.39 milliequivalents of $Na_2O$ per gram of catalyst; preferably it will be between 0.18–0.35 milliequivalents per gram of catalyst.

Satisfactory forms for adding the alkali are the conventional bases sodium hydroxide, sodium carbonate, sodium bicarbonate, sodium sesquicarbonate, and the like. Also sodium silicate, sodium aluminate, sodium acetate and the like which do not affect significantly the final composition of the catalyst can be used.

Also, according to the invention, the catalyst or contact mass employed, described herein, has been found suitably to be regenerated by the following procedure. The process of regeneration comprises purging the used catalyst with steam for about 1 hour (150 grams per hour when using 280 milliliter portions of alumina in a 1¼ inch stainless steel pipe reactor having a ¼" diameter axial thermowell—or with nitrogen at 8 standard cubic feet per hour). Then adding air to the purged fluid to provide approximately 0.5 volume percent oxygen, continuing the treatment for about 1 hour, then raising the oxygen concentration to about 1%, continuing treatment for another hour and raising the oxygen concentration to about 2% and maintaining this concentration until the combined concentration of carbon monoxide and carbon dioxide in the effluent has fallen to about 0.05%, cutting out the air while continuing to purge for about 1 hour before resuming addition of olefin.

It is important that the regeneration procedure be carefully conducted and that an undesired temperature rise thereof be avoided. By observing the above-mentioned procedure for the regeneration a maximum temperature rise of only 22° C. was obtained in the burning zone during regeneration.

For best results the temperature rise is now preferred to be limited to not more than about 25° C. above the temperature of the catalyst, the catalyst just prior to regeneration being at a temperature of the order of about 316°–593° C. (600°–1100° F.).

One skilled in the art in possession of this disclosure, having studied same, will understand that the burning zone will be more sharply defined or limited as the temperature of the catalyst is higher at the start of oxidation.

In the operation of the present invention branched as well as normal olefins can be converted to equilibrium concentrations of 1-olefin, with increasing temperature.

The presently preferred feedstock to be treated with the catalyst of the invention is one comprising isomeric n-butene.

While desirable isomerization can be affected at the earlier given temperature it is now preferred to hold the temperature in the range of from about 316 to about 593° C. (600°–1100° F.).

Reaction pressure is not critically important. It can be subatmospheric, and preferably will not exceed about 200 psig to avoid bi-molecular condensation reactions that ultimately lead to excessive coke formation on the catalyst.

Contact time of reactants on the catalyst, expressed as liquid hourly space velocity (LHSV), can range between about 0.5–50. Preferably it will be between about 1 and 30.

This invention can be explained further with the aid of the following example.

EXAMPLE

Specimens of the commercially manufactured alumina gel, Alcoa H-151, sold as a desiccant, were used to demonstrate double bond isomerization of n-butenes. These were received as spheres, and they were used without alteration. Some properties of the specimens that are pertinent to this invention are summarized in Table I.

TABLE I

| Catalyst | Form | Si, Wt. % | $Na_2O$ meq/gm | Na, Wt. % | $Na_2O$, Wt. % | Surface Area, $m^2/g$ | Pore Vol., ml/g |
|---|---|---|---|---|---|---|---|
| A | ¼" sphere | 0.50 | .24 | 0.55 | .73 | 321 | 0.45 |
| B | ¼" sphere | 0.98 | .33 | 0.77 | 1.05 | 349 | 0.50 |
| C | ¼" sphere | 0.75 | .50 | 1.16 | 1.57 | 352 | 0.47 |

As earlier described, the runs were made using a 1¼" stainless steel pipe reactor having a ¼" diameter axial thermowell, with 280 ml portions of alumina. The reactor was heated in a 5-zone electric furnace. Catalyst was supported on stainless steel packing in the reactor.

Liquid butenes under nitrogen pressure were metered to the reactor via a preheater. After reaction the product was cooled, depressurized in two stages, and measured. Samples of the intermediately pressured product were fed to an on-stream GLC analyzer.

The procedure used to regenerate the alumina was as follows. At the end of a process cycle the reactor was depressurized, then purged for one hour with steam (150 g/hr) or with nitrogen (8 SCF/hr). Air was added to the purging fluid to provide 0.5 volume percent oxygen. After one hour oxygen concentration was raised to one percent; after the second hour it was raised to 2 percent and maintained until the combined concentration of carbon monoxide and carbon dioxide had fallen to 0.05 percent. Then the addition of air was stopped while purging continued for one hour. Finally the feeding of butene was resumed, purge gas flow was halted, and a new cycle was underway. A maximum temperature rise of 22° C. was observed in the burning zones during regeneration by this procedure.

Table II summarizes the results of runs made using catalysts A, B and C. All tests were made at a pressure of 120 psig and 6.5 LHSV. The feed for these runs was a $C_4$ stream from a fractionating column that contained from a few percent to about 25 percent n-butane. Analyses shown in Table II show the increase in iso-butene concentration produced by treatment with the catalyst being used. The thermodynamic equilibrium concentration of butene-1 in n-butenes is approximately 23% at 371° C. (700° F.), 26% at 427° C. (800° F.), and 28% at 482° C. (900° F.).

TABLE II

| Run | Catalyst | Temp., °C. | On-Stream Time, Hrs. | Butene-1 as % of n-butenes | iso-Butene as % of Butene-1 |
|---|---|---|---|---|---|
| RUNS ACCORDING TO THE INVENTION | | | | | |
| 1 | A | 405 | 1 | 23.4 | 0.19 |
|   | A | 405 | 5 | 22.6 | 0.15 |

TABLE II-continued

| Run | Catalyst | Temp., °C. | On-Stream Time, Hrs. | Butene-1 as % of n-butenes | iso-Butene as % of Butene-1 |
|---|---|---|---|---|---|
|  | A | 413 | 12 | 22.9 | 0.10 |
|  | A | 421 | 24 | 22.6 | 0.14 |
|  | A | 421 | 33 | 23.6 | 0.19 |
|  | A | 421 | 39 | 23.3 | 0.09 |
| 2 | A | 427 | 1 | 25.9 | 0.71 |
|  | A | 427 | 9 | 25.8 | 0.56 |
|  | A | 427 | 12 | 25.6 | 0.56 |
|  | A | 427 | 33 | 24.7 | 0.37 |
| 3 | A | 427 | 1 | 25.9 | 0.81 |
|  | A | 427 | 15 | 25.0 | 0.42 |
|  | A | 427 | 29 | 24.5 | 0.37 |
| 4 | A | 427 | 6 | 25.4 | 1.23 |
|  | A | 427 | 30 | 24.2 | 0.73 |
|  | A | 427 | 61 | 20.2 | 0.20 |
| 5 | A | 427 | 1 | 25.1 | 0.31 |
|  | A | 427 | 30 | 25.1 | 0.16 |
|  | A | 427 | 48 | 24.6 | 0 |
|  | A | 427 | 72 | 22.2 | 0 |
|  | A | 427 | 82 | 20.4 | 0.13 |
| 6 | B | 427 | 3 | 21.3 | 0.11 |
|  | B | 427 | 12 | 21.0 | 0.05 |
|  | B | 427 | 19 | 21.1 | 0 |
| 7 | B | 427 | 2 | 20.1 | 0.17 |
|  | B | 427 | 13 | 18.9 | 0.12 |
| RUNS NOT ACCORDING TO THE INVENTION ||||||
| 8 | C | 427 | 1 | 16.7 | 0 |
|  | C | 427 | 4 | 14.9 | 0 |
| 9 | C | 427 | 4 | 13.2 | 0 |

Except for the earliest runs, most measurements listed on Table II were made at about the same temperature, viz., 427° C., at which the equilibrium butene-1 concentration is about 26%. Catalyst A consistently produced butene-1 yields near that value except in runs 4 and 5 after it had been on-stream for 61 and 82 hours, respectively. In contrast catalyst B, which contained about fifty percent more sodium than catalyst A, yielded significantly less butene-1. Catalyst C, which contained more than twice the sodium of catalyst A, was appreciably less active than both specimens A and B. With only one exception the calculated iso-butene concentration in the butene-1 fraction was always less than one percent—evidence for low skeletal isomerization activity. The temperature for the type of results shown can be in the approximate range 400°–435° C.

The activated alumina H-151, a commercially available alumina, generally will have properties as described in Alcoa Chemicals, Activated and Catalytic Aluminas, Mar. 1, 1960, wherein the following information is given.

| Typical Properties | | |
|---|---|---|
| $Al_2O_3$ | % | 86 |
| $Na_2O$ | % | 1.0 |
| $Fe_2O_3$ | % | 0.15 |
| $SiO_2$ | % | 6.3 |
| $TiO_2$ | % | — |
| Loss on ignition (1100° C.) (after reactivation) | % | 6.2 |
| $CaCl_2$ | % | — |
| $CoCl_2$ | % | — |
| Form |  | Ball |
| Surface area, sq. meter/g |  | 350 |
| Bulk density, loose, lb/ft$^3$ |  | 52 |
| Bulk density, packed, lb/ft$^3$ |  | 55 |
| Specific gravity |  | 3.1–3.3 |
| Dynamic sorption (1) | % | 21.23 |
| Crushing strength (2) |  | 60 |
| (footnotes omitted) | | |

As evidenced by later-issued information, the Alcoa H-151 product varies somewhat in its typical properties. As evidenced by the data herein, see Catalyst A, B of Table I and the data obtained therewith, these are within the acceptable range of 0.41–1.22% $Na_2O$. However, Catalyst C, which contains 1.57 $Na_2O$, weight percent, is not within the said acceptable range.

Reasonable variation and modification are possible within the scope of the foregoing disclosure and the appended claims to the invention the essence of which is that an alumina gel as herein described and having the properties herein given, has been found in combination with certain specifically limited proportions of $Na_2O$ to be excellently suitable for the isomerization of normal and branched olefins to 1-olefins without undesirable cracking and/or skeletal isomerization.

We claim:

1. A process for shifting an internal double bond of a monoolefin having 4–20 carbon atoms to yield terminal olefin which comprises heating said monoolefin under isomerization conditions at an isomerization temperature in the approximate range 260°–650° C. (500°–1200° F.) sufficient to cause shifting of the double bond while avoiding substantial cracking or skeletal isomerization in presence of a catalyst or contact mass essentially comprising an activated alumina having a surface area in the approximate range of from about 300 to about 400 square meters per gram and containing sodium oxide in the approximate range 0.13–0.39 milliequivalents of $Na_2O$ per gram of catalyst, and silica in the approximate range 0.5–6.3 weight percent of the catalyst, the sodium oxide having been supplied in the catalyst composition using a compound of sodium which on calcination yields the oxide.

2. A process according to claim 1 wherein isomeric n-butenes comprise the monoolefin.

3. A process according to claim 2 wherein the $Na_2O$ is present in the approximate range 0.18–0.35 milliequivalents per gram of catalyst.

4. A process according to claim 3 wherein the feed to the process is a $C_4$ stream as can be obtained from a fractionating column and containing isomeric n-butene, from a few percent to about 25% n-butane, and from 0 to a few tenths of a percent of iso-butene.

5. A process according to claim 4 wherein the isomerization temperature is in the approximate range of from about 400° to 435° C.

* * * * *